United States Patent [19]

Kessler

[11] Patent Number: 4,996,146

[45] Date of Patent: Feb. 26, 1991

[54] RAPID STERILIZATION ENZYMATIC PROCESS WITH PERSISTENCE

[76] Inventor: Jack H. Kessler, 23 Carriage House Path, Ashland, Mass. 01721

[21] Appl. No.: 488,507

[22] Filed: Mar. 5, 1990

Related U.S. Application Data

[63] Continuation of Ser. No. 17,224, Feb. 20, 1987, abandoned.

[51] Int. Cl.$^5$ .................... C12Q 1/28; C12Q 1/18; A01N 25/00; C12N 7/06
[52] U.S. Cl. .................................... 435/28; 422/1; 422/29; 422/37; 424/94.4; 424/405; 435/31; 435/32; 435/238; 435/264
[58] Field of Search .................. 424/50, 51, 53, 94.4, 424/130, 150, 405, 408; 422/1, 29, 37; 435/28, 78, 236, 238, 239, 264, 267, 192, 31, 32

[56] References Cited

U.S. PATENT DOCUMENTS

| | | | |
|---|---|---|---|
| 4,473,550 | 9/1984 | Rosenbaum et al. | 435/78 |
| 4,476,108 | 10/1984 | Kessler et al. | 424/130 |
| 4,576,817 | 3/1986 | Montgomery et al. | 424/94 |
| 4,588,586 | 5/1986 | Kessler et al. | 424/130 |
| 4,597,975 | 7/1986 | Woodward et al. | 424/150 |
| 4,670,178 | 6/1987 | Huth et al. | 424/94.4 |
| 4,719,106 | 1/1988 | Shetty et al. | 424/150 |

FOREIGN PATENT DOCUMENTS

| | | | |
|---|---|---|---|
| 2004647 | 8/1971 | Fed. Rep. of Germany | 424/150 |
| 2718385 | 11/1978 | Fed. Rep. of Germany | 424/150 |
| 81/00207 | 2/1981 | PCT Int'l Appl. | 424/150 |
| 82/01469 | 5/1982 | PCT Int'l Appl. | 424/150 |

Primary Examiner—Esther L. Kepplinger
Assistant Examiner—Florina B. Hoffer

[57] ABSTRACT

An enzymatic sterilization system is disclosed which is effective against viruses and other organisms. Methods are disclosed to increase the rate of and reduce the cost for sterilization with this chemistry as compared to the prior art. Methods are disclosed to formulate a sterlizing chemistry which actively maintains a sterile environment over a defined period of time.

7 Claims, No Drawings

RAPID STERILIZATION ENZYMATIC PROCESS WITH PERSISTENCE

This application is a continuation of prior U.S. application Ser. No. 017224 filing date 02/20/87, abandoned.

TECHNICAL FIELD

This invention relates to a rapid sterilizing enzymatic process and composition for sterilizing an aqueous-based medium and may be used to inactivate viruses, rapidly sterilize diaphragms, polymer membranes, instruments and a process suitable for use as a douche.

BACKGROUND

The ability to render all pathogens found in the environment inactive has been defined as sterilization. The requirements for a sterilization process can and will vary dramatically depending upon the particular application of interest. The ability of a given process to inactive or kill bacteria, fungi, viruses and naturally found hydrated spores is adequate function to qualify as a sterilant in most real world applications.

The disinfecting properties of peroxidase reactions have been well known for many years. In 1924 Hanssen (F. S. Hanssen, Brit. J. Exptl. Pathol. 5, 271 (1924)) ascribed the bactericidal properties of fresh milk toward Bacillus to "oxidizing" enzymes. In 1931 Kojima (S. Kojima, J. Biochem. 14, 95(1931)) described the ability of peroxidase to "accentuate" the bactericidal properties of its substrates. U.S. Pat. Nos. 4,476,231; 4,473,550 and 4,588,586 describe methods, utilizing the disinfecting ability of peroxidase systems, which effect a bactericidal environment for contact lens material and which serve as disinfection protocols in applications involving the oral cavity. This specification describes peroxidase mediated viral inactivation, methods to increase the rate at which a peroxidase based system effects sterilization and methods to decrease the cost per unit volume of said sterilization. In addition, this application delineates formulations and methods of application for said formulations which results in a rapid sterilization due to a peroxidase based chemistry wherein said composition subsequently has a substantially increased ability to actively maintain a sterile environment over a defined period of time as compared to the art described in U.S. Pat. Nos. 4,476,231; 4,473,550 and 4,588,586.

DESCRIPTION OF THE INVENTION

U.S. Pat. Nos. 4,476,231; 4,473,550 and 4,588,586 describe bactericidal methods using a peroxidase based system at a pH between 6.8 and 7.2. As described in U.S. application Ser. No. 861,926 (1986), this peroxidase based system requires over one hour to kill Bacillus pumilus spores (GBL no. D-25) at a pH of 7.0; the time required to kill 50% of a population of Pseudomonas aeruginosa under identical conditions is about 90 seconds. The requirement for rapid sterilization of instruments, membranes, diaphragms and other surfaces is not consistent with the temporal characteristics inherent in the system described above. This application describes methods to increase the rate at which the sterilizing properties of a peroxidase based iodide containing system function.

The minimum amount of peroxidase, the most expensive component of the sterilizing system, required per ml to effect sterilization of all types of organisms at levels of 1 million organism per ml is about 0.03 mg/ml. The cost associated with this amount of peroxidase vitiates most commercial applications which require the sterilization of a volume of liquid much larger than 50 ml. This application describes methods to reduce the cost of sterilization per unit volume of a peroxidase based iodide containing system.

Many sterilization protocols require both the rendering of pathogens found in the environment inactive and the maintainance of said sterile environment for a defined period of time. The art described in U.S. Pat. Nos. 4,476,231; 4,473,550 and 4,588,586 does not teach the active maintainance of a newly sterilized environment in a sterile condition. This application defines formulations and methods of application for said formulations which results in two distinct properties: (1) a rapid sterilization due to the peroxidase catalyzed reaction and (2) an ability to actively maintain a sterile environment for an extended period of time.

DETAILED DESCRIPTION OF THE INVENTION

The prevalence of viral infection in today's environment and the dramatic consequences of some viral disease mandates viral inactivation as a requirement for any potential sterilization process. This application discloses the ability of a peroxidase based chemistry system to inactivate or kill viruses. This ability renders this system suitable for applications involving the sterilization of medical and dental instruments as inactivation of infective viral agents is a requirement for such uses. Additionally, the ability to inactivate viruses qualifies the peroxidase catalyzed sterilization system of this application to function, within the constraints of the environment, in applications involving the female urogenital tract. The pH of the female urogenital tract is acidic; it has been observed that the antiviral properties of the peroxidase based sterilization system of this application are maximal under acidic conditions and are therefore compatible with sterilizations involving the female urogenital tract.

The time required to effect a sterilization process constrains the potential applications of and influences user acceptance of said process. Accordingly it has been observed that it is possible to increase the rate of sterilization using a peroxidase based enzymatic chemistry as compared to the processes described in U.S. Pat. Nos. 4,476,231; 4,473,550 and 4,588,586. This increase in the rate of sterilization is effected by controlling the pH of the environment in which the peroxidase based enzymatic sterilization chemistry occurs. If the pH of the environment is controlled at a value between pH 4 and 6.5 the rate at which the peroxidase based enzymatic chemistry effects sterilization is substantially increased.

The integral components of the sterilization chemistry defined in this application are peroxidase, an iodide salt and a source of peroxide. By a greater than ten fold factor peroxidase contributes the most cost per unit volume in all sterilization protocols. The cost of peroxidase obviates or limits the commercial use of this chemistry as described in U.S. Pat. Nos. 4,476,231; 4,473,550 and 4,588,586 for applications where the volume of sterilizing agent required is greater than 50 ml. Among the many commercial houses which sell purified peroxidase there is a functionally meaningful range of specifications and cost. Nevertheless, the cost of this chemistry using the least expensive quality of enzyme from the least expensive source presently available is equal to or greater than $0.004 per ml. Applications involving the sterilization of medical and dental instruments often require 100-1000 ml of sterilant. Since there are other sterilizing agents, such as Sporicidin, presently available which cost less than $0.004 per ml, it is necessary to reduce the cost associated with the peroxidase based chemistry described in U.S. Pat. Nos. 4,476,231; 4,473,550 and 4,588,586 in order for it to have commercial utility in many areas.

It has been discovered that the amount of peroxidase required to inactivate bacteria, viruses, spores and fungi using the peroxidase based sterilization chemistry of this application can be substantially reduced if the pH of the environment in which the sterilization occurs is kept between pH 4.0 and 6.5. This pH range does not correspond exactly to the pH optimum observed with many of peroxidase's substrates and the reason for the unexpected beneficial effect upon sterilization therefore may be related to interactions of the byproducts of the enzymatic rection. There is a ten fold reduction in the amount of enzyme required for an equivalent sterilization at a pH of 5 as compared to that at a pH of 7.0. This ten fold reduction in the amount of enzyme required for sterilization at this lower pH translates into a ten fold reduction in materials cost per ml of sterilizing chemistry.

The active maintainance of a sterile environment for a defined period of time once an environment has been sterilized is often needed. The art taught in U.S. Pat. Nos. 4,476,231; 4,473,550 and 4,588,586 does not teach the active maintainance of a sterile environment for a prolonged period of time. An ostensibly obvious method of actively maintaining a sterile environment when utilizing the peroxidase/peroxide based chemistry of this application is to increase the concentration of peroxide to about 3% at which concentration it is both bactericidal and virucidal. The difficulty with this approach is that once the concentration of peroxide is elevated to concentrations near or above 0.03% the ability of the peroxidase/peroxide based chemistry of this application to function upon a substantially simultaneous admixture of its components is diminished or eliminated. That is, at peroxide concentrations higher than 0.03% it is the disinfecting ability of peroxide which contributes bactericidal efficacy and not the reaction due to peroxidase.

It has been discovered that adding high concentrations of iodide to peroxidase prior to or coincident with the addition of hydrogen peroxide allows the peroxidase mediated sterilization chemistry to function at peroxide concentrations that are substantially above those otherwise possible. At a pH of 4 the activity of peroxidase does not substantially change between peroxide concentrations of 0.00003% and 0.003%; however, a peroxide concentration of 0.03% typically reduces the rate of a peroxidase catalyed reaction by over 50%. This inhibition of peroxidase and concomitant reduction in sterilization effected by the peroxidase based chemistry of this application can be overcome by increasing the concentration of iodide added to the reaction mixture. It is imperative that iodide be used as the donor molecule when attempting to overcome the deleterious effects of elevated peroxide concentration as iodide is both an effective sterilizing donor molecule for peroxidase as well as a donor molecule with very high solubility properties. The solubility properties of the donor molecule are critical as a molar ratio of iodide to peroxide must be maintained to mitigate the deleterious effects of elevated peroxide concentration on peroxidase.

The peroxidase of this invention is identified by the International Union of Biochemistry and the International Union of Pure and Applied Chemistry, Enzyme Commission identification No. E.C. 1.11.1.7. Peroxidase can be obtained from a wide variety of sources. The least expensive peroxidase suitable for this application is horse-radish peroxidase although theoretically lactoperoxidase can also be used. Commercially obtained peroxidase comes lyophilized as a dry powder.

The donor molecule of this invention is iodide. Suitable sources of iodide for this invention include sodium iodide and potassium iodide although many other salts of iodide are also suitable. Any compound which yields iodide ions upon dissolution is potentially suitable for this application as long as the cation component of said salt does not introduce deleterious factors to the process. The simple salts of iodide have the advantage of being inexpensive and exhibiting essentially infinite shelf life both in solid and liquid form.

The oxidant of this invention is hydrogen peroxide or a compound which yields hydrogen peroxide upon dissolution in water or an appropiate carrier. Alternatively methyl peroxide can be formulated in the product. Suitable materials for this use include hydrogen peroxide, methyl peroxide, metal peroxides, percarbonates, persulphates, perphosphates, peroxyesters, urea peroxide, peroxyacids, alkyperoxides, acylperoxides and perborates. Mixtures of two or more of these substances can also be used.

The four integral components of this invention—a peroxide source, buffering components to control the pH between 6.5 and 4.0, peroxidase and an iodide salt—must be stored in a fashion such that the enzymatic reaction is not initiated until the sterilizing properties of the chemistry are desired. It is acceptable to combine any two of the enzyme components of this system and isolate them from the third component in order to effect this end. It is also possible to store the components of this system in a powder or pill form such that the enzymatic reaction is precluded until such time as said powder or pill is admixed in a suitable carrier. In cases where it is desirable to actively maintain a sterile environment for a defined period of time by running the reaction at elevated peroxide concentrations it is preferred to add the peroxide component of the reaction last. For instance, one could combine high concentrations of iodide with peroxidase in a suitable carrier and add peroxide to said carrier as a last step. If a powder or pill is desired for use in an application where it is required to actively maintain a sterile environment for a defined peroiod of time it is possible to add a formulation wherein iodide and enzyme dissolve rapidly and peroxide is released slowly over time.

PREFERRED EMBODIMENT OF THE INVENTION

A prerequisite for the storage of any formulation prior to use is the prevention of the three enzymatic components of this system (a peroxide source, peroxidase and an iodide salt) from combining under conditions wherein the catalytic process is initiated. That is, it is imperitive that the storage of the enzymatic components will not allow the depletion of said components until the enzymatic reaction is purposely initiated immediately prior to use. If the enzymatic components are permitted to interact before intended for use, the inevitable depletion of the enzyme's substate molecules (peroxide/iodide) will result and thereby attenuate the effectiveness of the formulation. It is acceptable to combine any two of the enzymatic components of this system and isolate them from the third component in order to effect this end. That is, if it is practical to separate any one of the three enzymatic components from the other two prior to initiation of the enzymatic reaction, it will serve the prupose of preserving the integrity of the formulation. Alternately it is possible to have two separate mixtures which contain any two of the enzymatic components of the system in any combination and to combine these two mixtures immediately prior to use.

It is also possible to store the four components of this system in a powder or pill form such that the enzymatic reaction is precluded until such time as said powder or pill is admixed in a suitable carrier. In cases where it is desirable to actively maintain a sterile environment for a defined period of time by running the reaction at elevated peroxide concentrations it is preferred to add the peroxide component of the reaction last. For instance, one could combine high concentrations of iodide with peroxidase in a suitable carrier and add peroxide to said carrier as a last step. If a powder or pill is desired for use in an application where it is required to actively maintain a sterile environment for a defined peroiod of time it is possible to add a formulation wherein iodide and enzyme dissolve rapidly and peroxide is released slowly over time.

At a peroxide concentration of 0.30 molar peroxidase exhibits twice the activity at a peroxide to donor molecule ratio of 0.5 as compared to 0.125 using a typical donor molecule. At a 0.3% peroxide concentration peroxidase expresses twice its activity at a donor to peroxide ratio of 1 as compared to 0.25. The relationship of enzyme activity versus peroxide/iodide concentrations varies across the pH range defined in this application. It is desired to maintain a molar ratio of iodide to peroxide of between 0.5 and 1.0 when the concentration of peroxide is at or above 0.03%. Too high a ratio of iodide to peroxide establishes substrate conditions such that the majority of peroxide can be consumed, thereby obviating an active maintainance of the sterile environment. Since an enzymatic cycle consumes two molecules of iodide for every molecule of peroxide an equimolar concentration of substrates—donor molecules and peroxide—at millimolar or above concentrations will result in an effective equilibrium concentraion of 50% of the initial peroxide concentration.

The preferred pH range in which to run the sterilizing enzymatic chemistry of this application is between pH 6.5 and 4.0. The rate of sterilization is increased as the pH is lowered from pH 6.5; the sterilization occurs more rapidly at pH 5.5 than at pH 6.0. If the pH is lowered too far, the enzyme will not function as rapidly and the environment will present a greater possibility for causing irritation to human tissue which comes in contact with either the sterilizing chemistry or devices which have come in contact with the sterilizing chemistry. The reduction in the amount of enzyme required to effect sterilization between pH 6.5 and 4.0 is as much as ten fold. The reduction in the amount of enzyme required to effect sterilization between pH 6.5 and 4.0 is a function of the pH which is selected and is less at a pH of 5.5 than 6.5. The optimum pH at which to run the sterilizing chemistry of this application cannot be identified unless consideration is given to material compatibility and the organoleptic constraints for a particular application. For instance, a hollow fiber dialyzer of the type used in kidney dialysis could be composed of polymethylmethacrylate, polypropylene, polyacrylonitrile, polyamide, or cellulose acetate; depending upon which polymer the dialyzer's membranes were composed of it might be necessary or preferable to run the sterilizing ezymatic chemistry of this application at a pH of 6.0 ranther than 5.0. Althought pH 6.0 is not the pH which exhibits the most rapid rate of sterilization or which requires the least amount of enzyme per ml it could be that a lower pH would be deleterious to the sensitive membranes of a particular hollow fiber dialyzer or that a lower pH required a great deal more sterile saline to flush the remnants of the sterilizing chemistry from the hollow fiber dialyzer thereby incurring additional cost.

EXAMPLES

1. Bacteriophage T2 and $0 \times 174$ was grown in $E.\ coli$ strain B and $E.\ coli$ strain C respectively using a kit from Carolina Biological Supply Company (cat. no. 12-4315). To 800 ul of T2 and $0 \times 174$ was added 10 ul of potassium iodide (40 mg/ml), 10 ul of 0.03% hydrogen peroxide, and 10 ul of peroxidase (5 mg/ml in 10 mM phospate, pH 7.0). The suspension was irrcubated for five minutes. T2 and $0 \times 174$ (200 ul) treated and untreated with peroxidase were added to suspensions of warm agar containing $E.\ coli$ strain B and $E.\ coli$ strain C respectively. The agar mixtures were poured onto plates and spread evenly over the surfce. After solidifying at room temperature the plates were incubated at 37 degrees centigrade. The plates were checked for cell lysis. The viruses which were treated with the peroxidase based sterilizing chemistry of this application did not exhibit any cell lysis(plaques). The bacteria on the control plates exhibited plaque formation. This experiment indicates that this chemistry is capable of inactivating viruses.

2. Bacteriophage T2 was grown in $E.\ coli$ strain B and titered to 1000 pfu/ml when assayed by the double agar layer technique in 100 mm petrie dishes. To 800 ul of T2 was added 10 ul of potassium iodide (40 mg/ml), 10 ul of 0.03% hydrogen peroxide, and 100 ul of 100 mM posphate buffer at pH 5.0 or 7.0. Ten microliters of peroxidase was added; the stock solution of peroxidase (5 mg/ml in water) was diluted so that the lowest amount of peroxidase per ml in the final mixtures was 0.007 mg/ml. The suspensions were incubated for five minutes. Aliquots of the suspensions were removed and added to suspensions of warm agar containing $E.\ coli$ strain B. The agar mixtures were poured onto plates and spread evenly over the surfce. After solidifying at room temperature the plates were incubated at 37 degrees centigrade. The plates were checked for plaque formation. At a pH of 5.0 no plaques were formed; at a pH of 7.0 plaque formation could was observed at a peroxidase concentration of 0.070 mg/ml. This experiment indicates that it is possible to effect sterilization with significantly less peroxidase at pHs below 7.0.

3. Two identical scapels and forceps were autoclaved and placed on a shaking platform in a glass vessel containing a suspension of T2 virus in $E.\ coli$ strain B at 10,000 pfu/ml. Two of the instruments were removed and placed in a mixture containing 50 ml of sodium phosphate (pH 5.5), 500 ul of KI (40 mg/ml) and 500 ul hydrogen peroxide (0.3%). Peroxidase at 5 mg/ml was added (500 ul) and the solution was gently shaken; the controls were treated identically except for the omission of peroxidase. The reaction was allowed to proceed for 10 minutes and then 20 ml of sodium fluoride was added (2.3 G/L). The scapels and forceps were removed from solution and placed in soft agar containing E. coli strain B. The agar was allowed to solidify at room temperature and then incubated at 37 degrees centigrade in a standing incubator and checked for plaque formation. The controls exhibited plaque formation while the samples treated with peroxidase did not form any plaques.

4. An Ortho All-Flex diaphragm was cut into small sections. Sections of a diaphragm were incubated at 37 degrees centigrade in sterile saline solutions containing 1000 pfu/ml T2 virus or 1 million per ml S. monocytogenes or 1 million per ml C. jejuni. The diaphragm sections were removed and placed in a mixture containing 500 ul of KI(40 mg/ml), 500 ul of peroxide (0.03%) and 25 ml of 0.1M Tris (pH 5.0). Peroxidase was added (500 ul:5 mg/ml/water) and the solutions were shaken gently at room temperature for 5 minutes. Control reactions did not receive peroxidase. The diaphragm sections were removed and placed under appropiate conditions to monitor the viability of each type of organism (Salmonella, 37 degrees C. agar plates: Campylobacter, 42 degrees C. antibiotic/sheep blood plates: T2, double agar layer technique). No plaque formation was observed for T2 and neither Salmonella nor Campylobacter formed any colonies whereas controls exhibited viable organisms in each instance.

5. *Pseudomonas aeruginosa* and *Salmonella monocytogenes* were used to determine the relative rate of sterilization at pH values of 4.0, 5.0, 6.0 and 7.0. Overnight cultures of these organisms were grown and suspended in a solution which contained 10 ul KI(40 mg/ml), 10 ul peroxide (0.03%), 50 mM citrate at the indicated pH and 10 ul peroxidase (5 mg/ml). Cells were removed from this solution at various times, serially diluted tenfold and aliquots were plated out in order to determine the number of viable colonies per ml. The Stumbo equation was used to calculate D10 values at the different times points. The increased rate of inactivation of these organisms at a pH between 4.0 and 6.5 as compared to the rate of inactivation at pH 7.0 is clearly indicated by the data below.

| | *Salmonella monocytogenes* | | | |
|---|---|---|---|---|
| TIME (sec) | pH 4.0 D10 | pH 5.0 D10 | pH 6.0 D10 | pH 7.0 D10 |
| 0 | — | — | — | — |
| 20 | 26 | 11.9 | 41 | 43 |
| 40 | 33 | — | 39 | 42 |

| | *Salmonella monocytogenes* | | | |
|---|---|---|---|---|
| TIME (sec) | pH 4.0 D10 | pH 5.0 D10 | pH 6.0 D10 | pH 7.0 D10 |
| 80 | 36 | — | 37 | 48 |

| | *Pseudomonas aeruginosa* | | | |
|---|---|---|---|---|
| TIME (sec) | pH 4.0 D10 | pH 5.0 D10 | pH 6.0 D10 | pH 7.0 D10 |
| 0 | — | — | — | — |
| 45 | — | 27.8 | 40 | 70.3 |
| 90 | — | 28.4 | 37 | 68.7 |
| 135 | — | — | 34 | 65 |

What is claimed is:

1. A method for sterilizing an aqueous-based medium containing pathogens consisting essentially of the steps of: selecting four components including a source of peroxide, a peroxidase selected from the class contained in the E.C. #1.11.1.7, a salt of iodide, and buffering means selected to render the pH of said aqueous-based medium between a pH of about 6.5 and 4.0; storing said four components in a nonreacting state and admixing the four components in said aqueous-based medium under conditions and for a time sufficient to cause a catalyzed reaction for generating sterilizing agents from said source of iodide to sterilize said aqueous-based medium.

2. A method for sterilizing an aqueous-based medium, as defined in claim 1, wherein the molar ratio of iodide to peroxide is between 0.5 and 1.0.

3. A method for sterilizing an aqueous-based medium, as defined in claim 2, wherein the concentration of peroxide in said medium is between 0.0003% and 0.03%.

4. A method for sterilizing an aqueous-based medium, as defined in claim 3, wherein said salt of iodide is selected from the class consisting of sodium iodide and potassium iodide.

5. A method for sterilizing an aqueous-based medium, as defined in claim 4, wherein said four components are maintained inactive until introduced into said aqueous-based medium.

6. A composition for sterilizing an aqueous-based medium consisting essentially of a source of peroxide, a peroxidase selected from the class contained in the E.C. #1.11.1.7, a salt of iodide and buffer means to render the pH of said aqueous-based medium between a pH of about 6.5 and 4.0 said composition containing the ingredients in amounts sufficient to sterilize an aqueous-based medium.

7. A composition, as defined in claim 6, wherein peroxide is present in said composition at a concentration of between 0.0003% and 0.03%.

* * * * *